United States Patent
Venkatraman et al.

(10) Patent No.: US 9,987,367 B2
(45) Date of Patent: Jun. 5, 2018

(54) HYALURONIC ACID-BASED DRUG DELIVERY SYSTEMS

(71) Applicant: NANYANG TECHNOLOGICAL UNIVERSITY, Singapore (SG)

(72) Inventors: Subramanian Venkatraman, Singapore (SG); Tina Tzee Ling Howden, Singapore (SG); Leonardus Kresna Widjaja, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days. days.

(21) Appl. No.: 14/426,353

(22) PCT Filed: Sep. 6, 2013

(86) PCT No.: PCT/SG2013/000389
§ 371 (c)(1),
(2) Date: Mar. 5, 2015

(87) PCT Pub. No.: WO2014/039012
PCT Pub. Date: Mar. 13, 2014

(65) Prior Publication Data
US 2015/0250891 A1    Sep. 10, 2015

Related U.S. Application Data

(60) Provisional application No. 61/697,296, filed on Sep. 6, 2012.

(51) Int. Cl.
*A61K 47/36*    (2006.01)
*A61K 9/16*    (2006.01)
(Continued)

(52) U.S. Cl.
CPC ........... *A61K 47/36* (2013.01); *A61K 9/0014* (2013.01); *A61K 9/0019* (2013.01); *A61K 9/06* (2013.01);
(Continued)

(58) Field of Classification Search
None
See application file for complete search history.

(56) References Cited

U.S. PATENT DOCUMENTS 7,816,316 B2    10/2010  Lau
9,956,195    *    5/2018  Venkatraman ....... A61K 31/216
(Continued)

FOREIGN PATENT DOCUMENTS

JP    H10-67687    3/1998
JP    2004-323454    11/2004
(Continued)

OTHER PUBLICATIONS

Y Yeo, T Ito, E Bellas, CB Highley, R Marini, DS Kohane. "In Situ Cross-linkable Hyaluronan Hydrogels Containing Polymeric Nanoparticles for Preventing Postsurgical Adhesions." Annals of Surgery, vol. 245, No. 5, May 2007, pp. 819-824.*

(Continued)

*Primary Examiner* — Isaac Shomer
(74) *Attorney, Agent, or Firm* — Ladas & Parry, LLP

(57) ABSTRACT

The present invention relates to novel hyaluronic acid (HA) hydrogels comprising vesicles loaded with a drug or a protein or a nucleic acid. The new HA hydrogels provide sustain release formulations that are useful for several clinical and surgical applications, including but not limited to ophthalmology (e.g. glaucoma, corneal, ocular inflammatory, vitreoretinal and medical retinal diseases) and dermatological conditions.

15 Claims, 11 Drawing Sheets

(51) Int. Cl.
- A61K 9/127 (2006.01)
- A61K 31/5575 (2006.01)
- A61K 31/7105 (2006.01)
- A61K 31/513 (2006.01)
- A61K 9/00 (2006.01)
- A61K 9/06 (2006.01)
- A61K 31/216 (2006.01)
- A61K 31/728 (2006.01)
- A61K 9/51 (2006.01)

(52) U.S. Cl.
CPC ............ *A61K 9/127* (2013.01); *A61K 9/1647* (2013.01); *A61K 9/5161* (2013.01); *A61K 31/216* (2013.01); *A61K 31/513* (2013.01); *A61K 31/5575* (2013.01); *A61K 31/7105* (2013.01); *A61K 31/728* (2013.01); *Y10S 977/773* (2013.01); *Y10S 977/906* (2013.01); *Y10S 977/907* (2013.01)

(56) References Cited

U.S. PATENT DOCUMENTS

| | | | | |
|---|---|---|---|---|
| 2001/0005501 | A1* | 6/2001 | Marriott | A61K 9/0014 424/1.21 |
| 2003/0157161 | A1* | 8/2003 | Hunter | A61K 9/0019 424/450 |
| 2004/0067540 | A1* | 4/2004 | Lassota | A61K 49/0004 435/7.23 |
| 2007/0141134 | A1* | 6/2007 | Kosak | A61K 31/4706 424/450 |
| 2008/0107738 | A1* | 5/2008 | Philips | A61K 9/0048 424/489 |
| 2009/0226531 | A1 | 9/2009 | Lyons et al. | |
| 2010/0285113 | A1* | 11/2010 | Shoichet | A61K 9/0024 424/450 |
| 2015/0050332 | A1* | 2/2015 | Schubert | A61K 48/0016 424/450 |
| 2016/0175488 | A1* | 6/2016 | Klein | A61L 27/34 523/113 |

FOREIGN PATENT DOCUMENTS

| | | |
|---|---|---|
| JP | 2006-523731 | 10/2006 |
| WO | 2002/087563 A2 | 11/2002 |
| WO | 2004/046200 | 6/2004 |
| WO | 2004/092223 | 10/2004 |
| WO | 2005/054302 | 6/2005 |
| WO | WO 2008100044 A1 * | 8/2008 ............ A61K 8/345 |
| WO | 2010/140869 A2 | 12/2010 |
| WO | WO 2013021249 A1 * | 2/2013 ............ A61L 27/52 |

OTHER PUBLICATIONS

J Lee, KY Lee. "Injectable Microsphere/Hydrogel Combination Systems for Localized Protein Delivery." Macromolecular Bioscience, vol. 9, 2009, pp. 671-676.*
MN Collins, C Birkinshaw. "Comparison of the Effectiveness of Four Different Crosslinking Agents with Hyaluronic Acid Hydrogel Films for Tissue-Culture Applications." International Journal of Applied Polymer Science, vol. 104, 2007, pp. 3183-3191.*
JA Burdick, GD Prestwich. "Hyaluronic Acid Hydrogels for Biomedical Applications." Advanced Materials, vol. 23, 2011, pp. H41-H56.*
E Ruel-Gariepy, G Leclair, P Hildgen, A Gupta, J-C Leroux. "Thermosensitive chitosan-based hydrogel containing liposomes for the delivery of hydrophilic molecules." Journal of Controlled Release, vol. 82, 2002, pp. 373-383.*
Leach, J.B., et al. "Characterization of Protein Release From Photocrosslinkable Hyaluronic Acid-Polyethylene Glycol Hydrogel Tissue Engineering Scaffolds," Biomaterials, vol. 26, pp. 125-135, (2005).
Bajaj, G. et al., "Hyaluronic Acid-Based Hydrogel for Regional Delivery of Paclitaxel to Intraperitoneal Tumors", Journal of Controlled Release, vol. 158, pp. 386-392, (Dec. 2011).
Bae, S.E., et al., "Effect of Temporarily Controlled Release of Dexamethasone on in vivo Chondrogenic Differentation of Mesenchymal Stromal Cells," Journal of Controlled Release, vol. 143, pp. 23-30, (2010).
Lee, M., et al., "Biomimetic Apatite-Coated Alginate/Chitosan Microparticles as Osteogenic Protein Carriers," Biomaterials, vol. 30, pp. 6094-6101, (2009).
Liao, X., et al., "Preparation Poly (Lactide-Co-Glycolide) Microsphere of Bone Sialoprotein," Nano Biomed Eng., vol. 2, pp. 133-137, (2010).
International Search Report for PCT/SG2013/000389 dated Dec. 9, 2013.
Written Opinion of the International Searching Authority for PCT/SG2013/000389 dated Dec. 9, 2013.
International Preliminary Report on Patentability for PCT/SG2013/0003899 dated Mar. 10, 2015.
Extended European Search Report from corresponding European Patent Application No. 20130834865.1 dated Mar. 30, 2016.
Luo, et al. "Cross-linked hyaluronic acid hydrogel films: new biomaterials for drug delivery," Journal of Controlled Release, 2000, vol. 69, p. 169-184.
Office Action from corresponding Japanese Patent Application No. 2015-531047 dated Feb. 27, 2018 and its English translation.

* cited by examiner

HYALURONIC ACID-BASED DRUG DELIVERY SYSTEMS

CROSS-REFERENCE TO RELATED APPLICATION

This application is the U.S. National Stage of International Patent Application No. PCT/SG2013/000389, filed on Sep. 6, 2013, entitled "Hyluronic Acid-Based Drug Delivery Systems", which claims the benefit of priority under 35 U.S.C. §119(e) to U.S. Provisional Application No. 61/697,296, entitled "Hyaluronic Acid-Based Drug Delivery Systems", filed on Sep. 6, 2012, the entire disclosure of each is hereby incorporated by reference in their entireties for all purposes.

FIELD OF THE INVENTION

The invention relates to the use of hyaluronic acid (HA) hydrogel to deliver drugs such as small molecule or proteins or peptides or nucleic acids at a controlled rate for several clinical and surgical applications, including but not limited to ophthalmology (e.g. glaucoma, corneal, ocular inflammatory, vitreoretinal and medical retinal diseases) and dermatological conditions. In particular, the invention relates to a HA hydrogel comprising loaded vesicles dispersed in the HA hydrogel wherein the vesicles are loaded with one or more drugs, one or more proteins, or one or more nucleic acids. The drugs or proteins or nucleic acids are released in a controlled manner. In addition, the invention relates to various ways for preparing the HA hydrogel comprising the vesicles loaded with drugs or proteins or nucleic acids. The invention relates to a method for preparing the HA hydrogel comprising loaded vesicles dispersed therein.

BACKGROUND OF THE DISCLOSURE

It is well known that hyaluronic acid (HA), a naturally-occurring glycosaminoglycan (GAG), plays a key role in wound healing. HA has a range of naturally occurring molecular sizes from 100 to 10,000,000 Da. HA is implicated in water homeostasis of tissues, in the regulation of permeability of other substances by steric exclusion phenomena and in the lubrication of joints. HA also binds specifically to proteins in extracellular matrix, on the cell surface, and within the cells cytosol, thereby having a role in cartilage matrix stabilization, cell motility, growth factor action, morphogenesis and embryonic development and inflammation. Unmodified HA has many important application in drug delivery and surgery. For example, it is used as an adjuvant for ophthalmic drug delivery. In addition, HA has important application in the fields of visco-surgery, visco-supplementation and wound healing. HA is also a building-block for biocompatible and biodegradables polymers with application in drug delivery, tissue engineering and visco-supplementation.

Hydrogels are formed by crosslinked polymers and are able to absorb high quantity of water without being dissolved. HA hydrogels are physically or covalently cross-linked HA gel. HA molecules are generally functionalized to allow reaction with a cross linker. Crosslinked HA hydrogels for example have been prepared by crosslinking with molecules such as di-epoxy-butane, ethylene-glycol di-glycidyl-ether (EGDGE) or poly-glycol diglycidyl-ether (PEGDE).

HA hydrogels have been used for several application including drug delivery applications. They are able to provide sustained, local delivery of a variety of therapeutic agent. Use of HA as a scaffold material in hydrogel has been pursued due to the biocompatibility, low toxicity, lack of immune response and biodegradability of HA hydrogel.

Although HA hydrogels have been studied for drug delivery applications, the delivery rates are difficult to control. If a hydrophilic drug is incorporated into the hydrogel, the incorporation is easy (large amounts can be loaded), but release is also rapid. On the other hand, it is difficult to get large amounts of hydrophobic drugs into such hydrogels, for solubility reasons. Any un-dissolved drug will migrate to the surface of the hydrogel and release in a burst (within a day or two).

There is therefore the need to provide further and improved drug/protein/nucleic acid sustain delivery formulations that allow an efficient and localized controlled release of hydrophobic and hydrophilic drugs, proteins or nucleic acid, avoiding the above mentioned drawbacks.

SUMMARY OF THE INVENTION

The present invention addresses this need by providing new and improved controlled release drugs or proteins or nucleic acids formulation and methods to prepare the same.

In a first aspect, the present invention is directed to a hyaluronic acid (HA) hydrogel comprising loaded vesicles dispersed therein wherein the vesicles are loaded with drugs or proteins and peptides or nucleic acids ("loaded vesicles").

The loaded vesicles are selected from micelles, liposomes and/or particles such as microparticles or nanoparticles. Preferably, the micelles are made of amphipilic self-assembling molecules. Amphipilic self-assembling molecules are preferably selected from polymers including block-copolymers and surfactants. Preferably, the particles are selected from chitosan nanoparticles or microparticles and poly(lactic-co-glycolic acid) (PLGA) nanoparticles or microparticles. Preferably, the amount of loaded vesicles is the 1% to the 40% by weight of the whole HA hydrogel system (HA hydrogel including the loaded vesicles). More preferably, 1-20% by weight of the whole HA hydrogel system.

The drug is preferably selected from a hydrophobic or hydrophilic drug, more preferably it is selected from an antibiotic drug such as ciprofloxacin, a chemio-therapeutic drug such as paclitaxel or doxorubicin or 5-fluorouracil, a drug for the treatment of glaucoma or ocular hypertension such as latanoprost and an anti-scaring drug as 5-fluorouracil.

Proteins are preferably selected from the group of monoclonal antibodies, such as bevacizumab (Avastin) and ranibizumab (Lucentis), or similar therapeutic proteins.

Peptides are preferably natriuretic peptides, including C-type natriuretic peptide (C-NP), A-type natriuretic peptide (A-NP), chimeric natriuretic peptide (CD-NP), mutant atrial natriuretic peptide (M-ANP).

Nucleic acids are preferably selected from the group of RNA, siRNA, DNA, cDNA and plasmid DNA.

The HA hydrogel according to the present invention is preferably an HA hydrogel which is a covalently crosslinked HA hydrogel. The HA moieties (backbone) that form the hydrogel are functionalized with a functional group to be linked to a crosslinker. The crosslinker is any molecule suitable to act as a crosslinker in HA hydrogel preparation. The crosslinking is performed in the presence of loaded vesicles to provide the HA hydrogel of the invention. The functional group is any molecule or moiety or group that is attached, preferably covalently attached to the HA and is able to react with a crosslinker molecule to crosslink the functionalized HA and for the HA hydrogel. Alternatively, the functional group is any molecule or moiety or group that is attached, preferably covalently attached to HA and is able itself to act as a crosslinker to form HA hydrogel. Preferably, HA is functionalized with methacrylic acid or anhydride to give methacrylate-HA (HA-MA), HA is functionalized with adipic acid dihydrazide (ADH) to give HA-ADH, or HA is functionalized with lactic acid to give MeLAHA or with caprolactone to give MeCLHA. Preferably, the crosslinker molecule is polyethylene glycol diglycidyl ether (PEGDE). The crosslinking of HA-MA with PEGDE provides, in the presence of loaded vesicles, an HA hydrogel comprising the loaded vesicles dispersed therein according to the invention. Alternatively, the crosslinking of HA-ADH with PEGDE provides, in the presence of loaded vesicles, an HA hydrogel comprising loaded vesicles dispersed therein according to the invention.

Alternatively, in the functionalized HA the functionalizing group is the crosslinker. Preferably, the functionalized HA is selected from HA-MA and HA-ADH. The functional group MA may act as a crosslinker to form HA-MA hydrogel. The functional group ADH may act as a crosslinker to form HA-ADH hydrogel.

Preferably, the HA hydrogel is selected from an HA-MA hydrogel, HA-ADH hydrogel, HA-ADH crosslinked with PEGDE-hydrogel, HA-MA crosslinked with PGDE-hydrogel.

Preferably, the molar ratio of effectively functionalized HA to crosslinker (wherein the crosslinker is not the functional group itself) is in the range of 1:20 to 1:1, preferably 1:10, to 1:2, more preferably 1:5 to 1:2. Hence, preferably the amount of crosslinker added is from 2 to 10 times the moles of HA effectively functionalized. For example, for a system such as HA-ADH system a crosslinker (which is not ADH itself) is used. For example with HA-ADH the crosslinker PEGDE is used. Generally, PEGDE is used in a ratio of 2 to 10 times the moles of HA-ADH effectively functionalized. For example, if the degree of functionalization of HA-ADH is of 50% (i.e. 50% of the whole HA molecules have ADH) then 2 to 10 times this amount of PEGDE can be added.

In a second aspect, the present invention provides methods for preparing the HA hydrogel comprising the loaded vesicles dispersed therein according to the present invention. The method comprises a) providing a functionalized HA with a functional group/moiety suitable to be linked to a crosslinker and b) crosslinking the functionalized HA moiety optionally in the presence of a crosslinker, wherein the crosslinking occurs in the presence of loaded vesicles and wherein when the crosslinker is not present the functional group/moiety on the HA acts as a crosslinker. Preferably, the functionalized HA is selected from HA-MA or HA-ADH. Preferably, the crosslinker is selected from PEGDE. Preferably, when the functional group act as crosslinker, the functional group is MA.

According to the method of the invention, the loaded vesicles are mixed with the functionalized HA to form a mixture. The crosslinker is then added to said mixture and let crosslink to provide the HA hydrogel comprising the loaded vesicles dispersed therein. Alternatively, the loaded vesicles are mixed with the crosslinker and the functionalized HA is added subsequently.

In the embodiment wherein the crosslinker is not required, because the functional group/moiety of the HA functionalized moiety acts as crosslinker the mixture comprising the HA functionalized and the loaded vesicles is let crosslink. The functionalized HA can be added as freeze-dried functionalized HA to the solution comprising the loaded vesicles. The concentration of the functionalized HA in the solution comprising the loaded vesicles is preferably of 1% to 20% (w/v), more preferably 2% to 4% (w/v).

The crosslinking is a chemical reaction or a radical polymerization (crosslinking) preferably a photo-crosslinking. Preferably the photo-crosslinking is a UV photo-crosslinking that optionally occurs in the presence of a photoinitiator. An initiator such as Irgacure 2959 is used to start the crosslinking. The amount of initiator is of 3% to 15% by weight of the functionalized HA preferably 10% by weight of the functionalized HA. For example, the amount of initiator is of 3% to 15% by weight of HA-MA, preferably 10% by weight of HA-MA when HA-MA is used to prepare HA-MA hydrogel.

In a third aspect, the present invention is directed to an HA hydrogel comprising loaded vesicles dispersed therein obtainable with any of the methods of the present invention.

In a fourth aspect, the present invention is directed to an HA hydrogel comprising loaded vesicles dispersed therein as defined above for use as a medicament.

In a fifth aspect the present invention is directed to a pharmaceutical formulation comprising the HA hydrogel comprising loaded vesicles dispersed therein as defined above. The pharmaceutical formulation is for oral, topical, intravenous, subcutaneous, intraocular or intramuscular administration.

DESCRIPTION OF THE DRAWINGS

The invention will be better understood with reference to the detailed description when considered in conjunction with the non-limiting examples and the accompanying drawings, in which.

DETAILED DESCRIPTION

The present inventors have found that the incorporation of vesicles loaded with hydrophobic and/or hydrophilic drug or proteins or nucleic acids into HA hydrogel provides formulations that have a control release profile and do not present the drawback of the direct incorporation of hydrophilic/hydrophobic drug or protein or nucleic acid into an hydrogel (respectively: rapid release and release in a burst within a day or two).

Advantageously, the present inventors have discovered that a HA hydrogel comprising loaded vesicles dispersed therein provides a system with an improved controlled release profile when compared to a system wherein the drug or the protein or the nucleic acid is directly loaded in the HA hydrogel and when compared to a system wherein the drug or the protein or the nucleic acid is loaded in the vesicles and released from the vesicle alone (no HA hydrogel is present).

Hence, in an aspect the present invention is directed to HA hydrogel comprising loaded vesicles dispersed therein wherein the vesicles are loaded with one or more drugs, one or more proteins or one or more nucleic acids.

"Vesicles" are as defined herein small sack/bubble able to contain a drug/protein/peptide/nucleic acid and to release it at the desired physiological conditions. Preferably, vesicles according to the present invention are selected from liposomes or micelles or particles selected from nanoparticles and microparticles. The vesicles are prepared such that they are loaded with hydrophobic or hydrophilic drug, protein, peptide or nucleic acid. Preferably, the loaded vesicles are prepared before their incorporation into the HA hydrogel.

"Micelles" are made of self-assembling amphipilic molecules. Self-assembling amphipilic molecules spontaneously exist in a unique structure (micelles) beyond a certain concentration. This concentration is known as the "critical micelle concentration" (CMC). Self-assembling amphipilic molecules can be for example polymers and surfactants. Examples include surfactants such as ($C_{10}$-$C_{22}$ alkyl sulphate, $C_{10}$-$C_{22}$ alkyl betaine, $C_{10}$-$C_{22}$ alkyl trimethyl ammonium salts and $C_{10}$-$C_{22}$ alkyl glucosides and polymers, preferably block copolymers such as copolymers of PLGA (poly(lactide-co-glycolide) and PEG (polyethylene glycol), copolymers of polycaprolactone (PCL) and PEG, copolymers of polyethylene polylactic acid (PEG/PLA), copolymers of polyethylene glycol (PEG) and polypropylene glycol (PPG) (also known as polyethylene and polypropylene oxides). Copolymers of polyethylene glycol (PEG) and polypropylene glycol (PPG) are generally sold under the brand names of Pluronic®.

Figure 1:
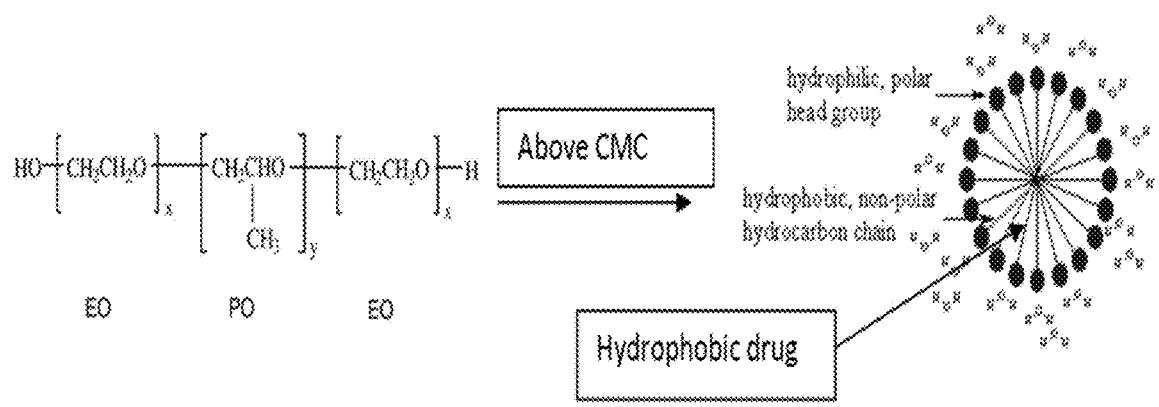
FIG. 1 shows a scheme of formation of micelles of PEG/PPG/PEG block copolymers and the load of a hydrophobic drug.

As said, a defined property of self-assembling amphipilic molecules such as Pluronic® is the ability of the molecules called "unimers" to self-assemble into micelles in aqueous solution. These "unimers" form a molecular dispersion in water at the molecule concentration below the CMC. At a concentration above the CMC, the unimers aggregate, forming micelles through a process called "micellization". For example with block copolymer, the driving force of the micellization is the hydrophobic interaction of the hydrophobic block (such as the PC) block in Pluronic®). The hydrophobic block self-assembles into the inner core of the micelles covered by the hydrophilic corona of the hydrophilic block (such as the EO block in Pluronic®). Pluronic® micelles are for example pictured as spheres composed by a PO core and an EO corona (FIG. 1). Additional micelle morphology including lamelles or rods can be formed. Generally, the micelles in dependence of the block polymer type used have different average hydrodynamic diameter. For example in dependence of the Pluronic® type used, the micelles can have an average hydrodynamic diameter ranging from 20 to about 80 nm. The number of block polymer forming one micelle is referred as the "aggregation number".

The center of the micelles is hydrophobic. If the hydrophobic drug or molecule is mixed into such polymers, the drug will reside in the hydrophobic core, as shown in the FIG. 1. The process of transfer of hydrophobic drug into the hydrophobic core (such as PO core) of the micellar solution is referred as "solubilization". The released of the drug occurs then by drug delivery mechanism.

Figure 2:
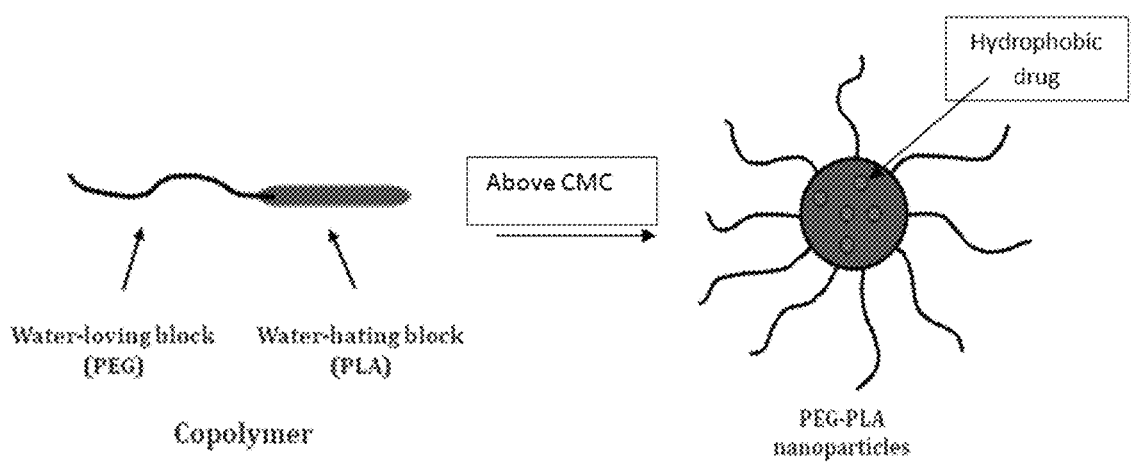
FIG. 2 shows a scheme of formation of micelles of PEG/PLA block copolymers and the load of a hydrophobic drug.

Polyethylene glycol-polylactic acid (PEG/PLA) copolymers are another example of copolymer forming micelles in an aqueous solution in a concentration above CMC. (FIG. 2). The present inventors have found that PEG/PLA copolymers are able to form micelles that incorporate hydrophobic drugs such as paclitaxel. The present inventor have found that to extract a greater level of release control, as well as overall drug loading, a significant amount of such micelles can be incorporated into HA hydrogels (~10-20% by weight), thus extending duration of drug release from a few days to a few months.

In an aspect of the invention, the micelles are made of self-assembling amphipilic molecules. Self-assembling amphipilic molecules can be selected from surfactants such as $C_{10}$-$C_{22}$ alkyl sulphate, $C_{10}$-$C_{22}$ alkyl betaine, $C_{10}$-$C_{22}$ alkyl trimethyl ammonium salts and $C_{10}$-$C_{22}$ alkyl glucosides or polymer, such as block copolymers. Preferably, the self-assembling amphipilic molecules according to the present invention are block copolymers. Preferably self-assembling amphipilic molecules are selected from copolymers of polyethylene glycol (PEG) and polypropylene glycol (PPG) such as Pluronic® and PEG/PLA; more preferably, Pluronic® is Pluronic® 127.

Figure 3A:
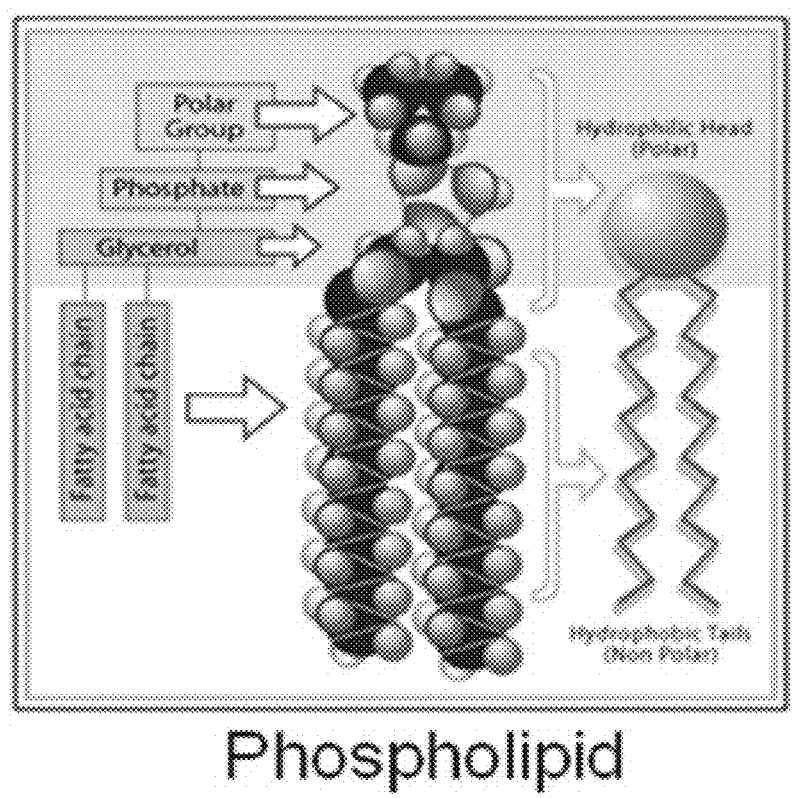
FIG. 3a is a picture of the phospholipid structure, the building block of liposomes.
Figure 3B:
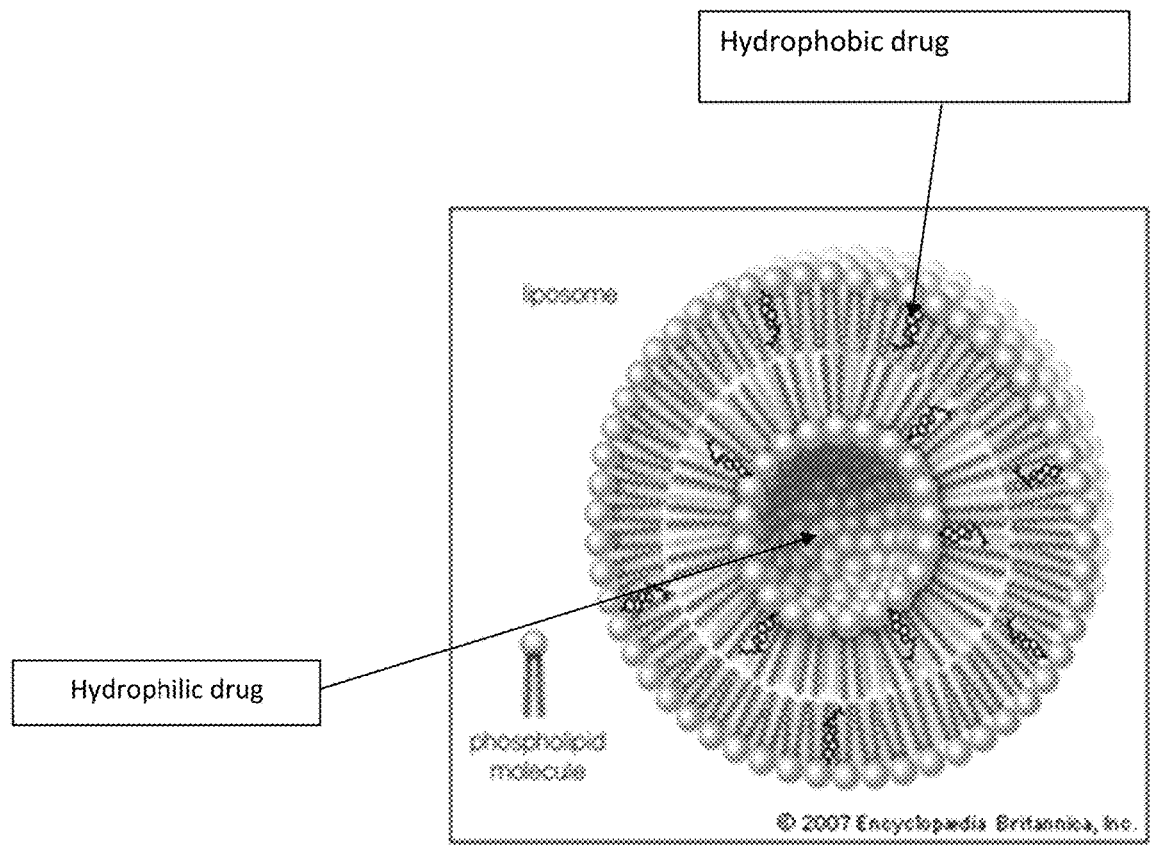
FIG. 3b shows the section of a liposome. It shows that a hydrophilic drug can be loaded in the liposome core and a hydrophobic drug can reside in the bilayer of the liposome.

"Liposomes" are vesicles composed by a lipid bilayer. Liposomes are often composed of phosphatidylcholine-enriched phospholipids. (FIG. 3). Both hydrophilic and hydrophobic drugs can be loaded into a liposome. Hydrophobic drugs are incorporated into the bilayer of the lipid vesicles, while hydrophilic drug are loaded into the "core" of the liposome (FIG. 3). For example, the present inventors have incorporated in a liposomal core the antibiotic ciprofloxacin a hydrophilic drug with a good loading and control release. A further release control has been achieved when such loaded liposomes were mixed with HA hydrogel precursors and crosslinked. Additionally, the present inventors have incorporated in the liposomal bilayer hydrophobic drug such as latanoprost. The loaded liposomes were further incorporated in the HA hydrogel precursors prior to the HA hydrogel crosslinking. The hydrogel precursors were let forming the HA hydrogel. The incorporation of liposomes into HA hydrogel further increase the control release of the drug.

In another embodiment, both hydrophobic and hydrophilic drugs can be loaded into the same liposome. The hydrophobic drug is in the bilayer part of the liposome by passive loading and the hydrophilic drug is in the core of the liposome by active loading.

Liposomes are preferably selected from EPC (or EggPC) liposomes, 1-Palmitoyl-2-oleoylphosphatidylcholine (POPC) based liposome and 1,2-dimyristoyl(d54)-sn-glycero-3-phosphocholine (DMPC) based liposome.

Particles according to the present invention are non-self-assembling particles in the size (diameter) range of 5 nm to 50 μm. Particles are defined as nanoparticles or microparticles in dependence of their size (diameter) range. Generally, nanoparticles have a size range from 5 nm to 250 nm. Microparticles have a size range >250 nm to 50 μm. Nanoparticles and microparticles are prepared by forming a complex between a drug, preferably a hydrophilic drug, with anionic or cationic species and then forming the nanoparticles. Anionic species used to prepare nanoparticles and microparticles are for example poly styrene sulfonate or poly-acrylic acid, cationic species are for example chitosan.

By way of a non-limiting example: drugs such 5-Fluorouracil (5-FU)

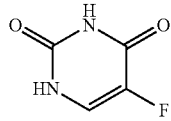

will dissolve in NH$_4$OH and exists as negative ions at high pH and as positive ions at lower pH. Therefore, such drugs may be complexed with anionic species (e.g., poly styrene sulfonate or poly-acrylic acid) at low pH to form complexes that can be more efficiently loaded into hydrogels compared to pure drug. At a higher pH, these drugs can be complexed with cations such as chitosan.

Hence, for hydrophilic drug, the present invention also comprises the preparation of complexed drug, for example with chitosan. The complexation using chitosan is followed by nano- or microparticles formation. The formed nanoparticles or microparticles are mixed into the HA hydrogel precursors which are crosslinked. The release control is optimized. Drug types that can be loaded in chitosan nanoparticles or microparticles include 5-Fluorouracil (5-FU) used as a chemotherapeutic and anti-scarring agent. Nucleic acids such as siRNA; plasmid DNA can be loaded in nanoparticles or microparticles.

Nanoparticles or microparticles according to the invention are also poly(lactic-co-glycolic acid) (PLGA)-nanoparticles (NPs) or PLGA-microparticles (PLGA-MPs). PLGA-NPs or PLGA-MPs are loaded with a drug or protein or polypeptide or nucleic acid. The loaded PLGA-NPs or PLGA-MPs are then embedded in the HA hydrogel via polymerization of the HA hydrogel precursors. PLGA-NPs or PLGA-MPs may be prepared by double emulsion solvent evaporation. Double emulsion solvent evaporation method is disclosed for example in Liao X, Wang J, Wang J, Zhang H: Preparation poly(lactide-co-glycolide) microsphere of bone sialoprotein. Nano Biomed Eng 2010, 2: 133.

Nanoparticles according to the present invention have a diameter ranging from 5 nm to 250 nm, preferable 40 to 100 nm. Microparticles according to the present invention have a diameter ranging from >250 nm to 50 μm.

HA is an anionic, non-sulfated glycosaminoglycan. "HA hydrogel" as defined herein is a crosslinked HA networks. The crosslinking is a preferably a covalent crosslinking i.e. HA is covalently bonded to crosslinker molecules so as to create a polymer network. HA contains a number of hydrophilic groups that have affinity for water. HA hydrogels are prevented from dissolving due to the bonds formed between the HA chains via the crosslinkers. Hence, HA or HA chemically modified can form an HA hydrogels via polymerization (cross-linking).

HA molecule has carboxyl groups, acetamido groups and OH group that can be functionalized with a chemical group suitable for crosslinking. According to the present invention, functionalized HA is an "HA hydrogel precursor". The crosslinker is the other "HA hydrogel precursor". When the functionalized HA is crosslinked optionally in the presence of crosslinker molecules it forms a HA hydrogel. Examples of functionalized HA are adipic acid dihydrazide HA (HA-ADH), methacrylated HA (HA-MA), thiolated HA (HA-SH). HA-ADH can be synthesized and used for the preparation of HA-MA by reaction with methacrylic anhydride.

HA-ADH can be used for the preparation of thiolated HA (HA-SH) by reaction with Traut's reagent (imminothiolane). Other functionalized HA are MeLAHA and MeCLHA. Preferred functionalized HA are HA-MA and HA-ADH.

"Crosslinkers" or crosslinking reagents/agents are molecules that contain two or more reactive ends capable or chemically attaching to specific functional groups of HA or functionalized HA. Non limitative examples of cross linkers that can be used for preparing the HA hydrogel according to the present invention are: buthylene glycol diglycidyl ether (BDG), butanediol diglycidyl ether (BDDGE) or poly(ethyleneglycol) diglycidyl ether (PEGDE). Preferably, the cross linker is PEGDE, more preferably is PEGDE of formula:

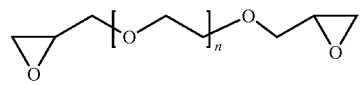

wherein n=1 to 50, preferably n=3-6.

The functionalized HA may be crosslinked in the presence of a crosslinker. As an illustrative example of this embodiment of the invention, HA-ADH and PEGDE or HA-MA and PEGDE in the presence of loaded vesicles may be crosslinked to give the HA hydrogel of the invention. The functionalized HA may be crosslinked in the presence of loaded vesicles and in the absence of a crosslinker as the functional group acts as crosslinker. As illustrative example of this embodiment of the invention, in the presence of loaded vesicles, HA-MA may be crosslinked, preferably is photo-crosslinked, to give a HA hydrogel (HA-MA hydrogel) having dispersed therein the loaded vesicles. Alternative as an illustrative example of this embodiment of the invention, in the presence of loaded vesicles, HA-ADH may be chemically crosslinked to give a HA hydrogel (HA-ADH hydrogel) having dispersed therein the loaded vesicles.

The amount of the loaded vesicles in the HA hydrogel may be in the range from 1% to 60% by weight of the whole HA hydrogel system (HA hydrogel plus loaded vesicles). Preferably, the amount of loaded vesicles is from 2% to 30% by weight of the whole HA hydrogel system, more preferably from 4% to 20% by weight of the whole HA hydrogel system.

The percentage/degree of functionalization on the HA backbone may depend on the functionalizing group. Typically, the percentage of functionalization is of 5 to 80% (i.e., 5 to 80 of the HA molecules have a functionalization/bear a functional group). Preferably the degree of functionalization of HA-ADH is of 20 to 80%, preferably the degree of functionalization of HA-MA is of 5% to 20%, more preferably 10%; preferably the degree of functionalization of HA-ADH is 45% to 50%.

Hence, the languages "functionalized HA" or "HA-ADH" or "HA-MA" etc. according to the present invention indicate a composition of HA comprising both functionalized and non-functionalized HA. The degree of functionalization is indicated by the percentage as disclosed above. The language "HA effectively functionalized" refers to the part of the "functionalized HA" which effectively bear the functional group. As an explanatory non limiting example, HA-MA with a 50% degree of functionalization means a composition wherein half molecules of HA are functionalized with MA and half molecules of HA are not functionalized. 50% of the HA molecules are effectively functionalized with MA. As an additional explanatory non limiting example, HA-MA with a 60% degree of functionalization means a composition wherein 60% of molecules of HA are functionalized with MA and 40% of molecules of HA are not functionalized i.e. are HA. 60% of the HA molecules are "effectively" functionalized with MA.

In a second aspect, the present invention is directed to a method for the preparation of HA hydrogel having loaded vesicles dispersed therein. The method comprises:
a) providing functionalized HA with a functional moiety wherein the functional moiety is for crosslinking;
b) crosslinking the functionalized HA optionally in the presence of a crosslinker;
wherein
the crosslinking occurs in the presence of loaded vesicles; and
wherein
when the crosslinker is not present the functional moiety acts as a crosslinker.

The functionalized HA is a HA hydrogel precursor. In the method of the invention the functionalized HA may be any functionalized HA suitable for the preparation of HA hydrogel. Functionalized HA are for example HA-MA, HA-ADH, HA-SH, MeLAHA and MeCLHA. Preferably, functionalized HA are selected from HA-ADH and HA-MA.

A cross linker molecule is a HA hydrogel precursor. "Cross linkers" or "crosslinking reagents" are molecules that contain two or more reactive ends capable or chemically attaching to specific functional groups of HA or functionalized HA: non limitative examples of crosslinkers that can be used for preparing the HA hydrogel according to the present invention are: butylene glycol diglycidyl ether (BDG), butanediol diglycidyl ether (BDDGE) or poly(ethyleneglycol) diglyCidyl ether (PEGDE). Preferably the crosslinker is PEGDE, more preferably is PEGDE of formula:

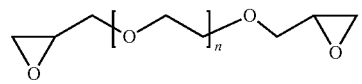

wherein n=50 to 400 wherein n=1 to 50, preferably n=3-6.

Vesicles, including micelles, liposomes and particles selected from nanoparticles and microparticles as disclosed above and loaded with a drug or protein or peptide or nucleic acids are used in the method of the invention to prepare the HA hydrogel comprising loaded vesicles dispersed therein.

The crosslinking reaction can be a chemical crosslinking for example via condensation or addition reaction or a radical polymerization wherein the polymerization (crosslinking) involves the formation of radical through some initiator source such as light, temperature or redox-reaction. Preferably, the radical polymerization (crosslinking) occurs via photo-polymerization (photo-crosslinking). Typically, UV radiation is used for photo-crosslinking. Typically, a photo initiator, such as Irgacure 2959, is present in the solution containing the HA hydrogel precursors and the loaded vesicles when the HA hydrogel is formed via photo-crosslinking.

Figure 10:
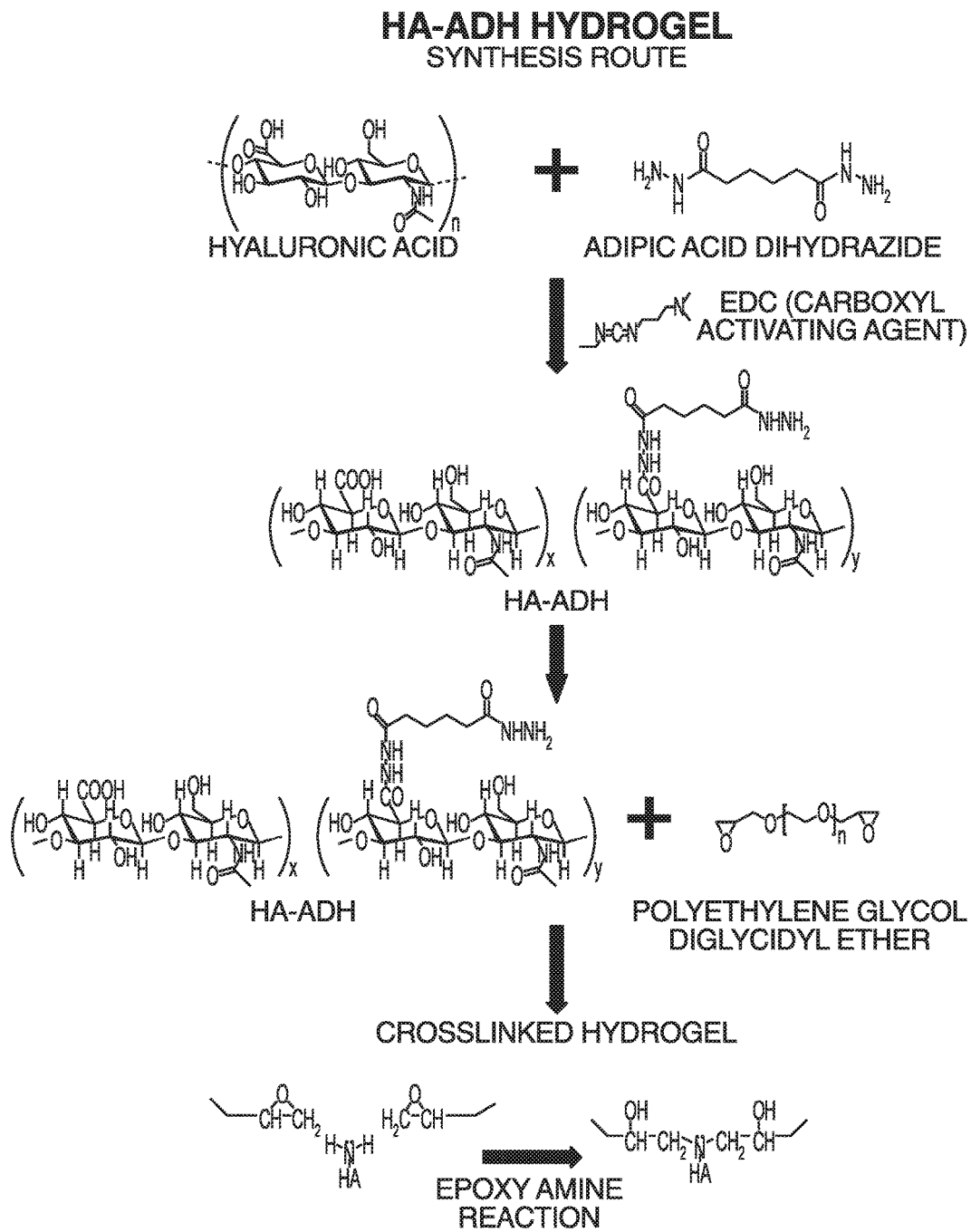
FIG. 10 shows an embodiment of an HA-ADH hydrogel synthesis route.

The conversion of an OH group to aldehyde of HA using adipic acid dihydrazide (ADH) followed by reaction with ethylene dicarbodiimide (EDC) to yield a reactive functional group in the HA backbone (HA-ADH) can be used in the method of the invention. The hydrogel is then form by crosslinking in the presence of a crosslinker such as PEDGE according to the synthesis route shown in FIG. 10.

HA-ADH HYDROGEL SYNTHESIS ROUTE

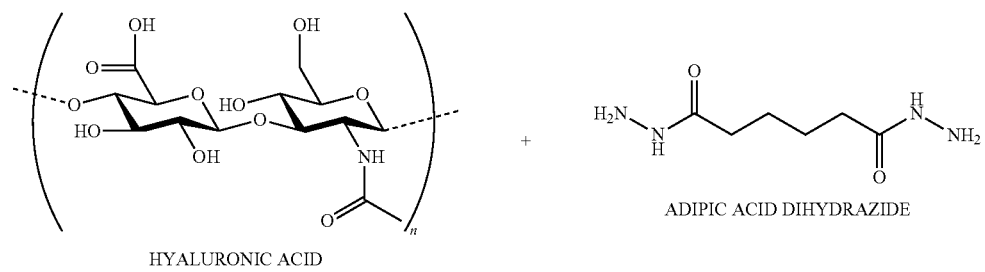

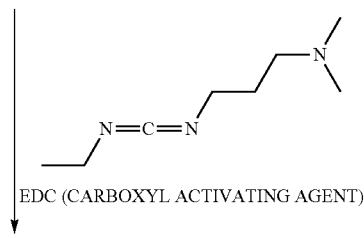

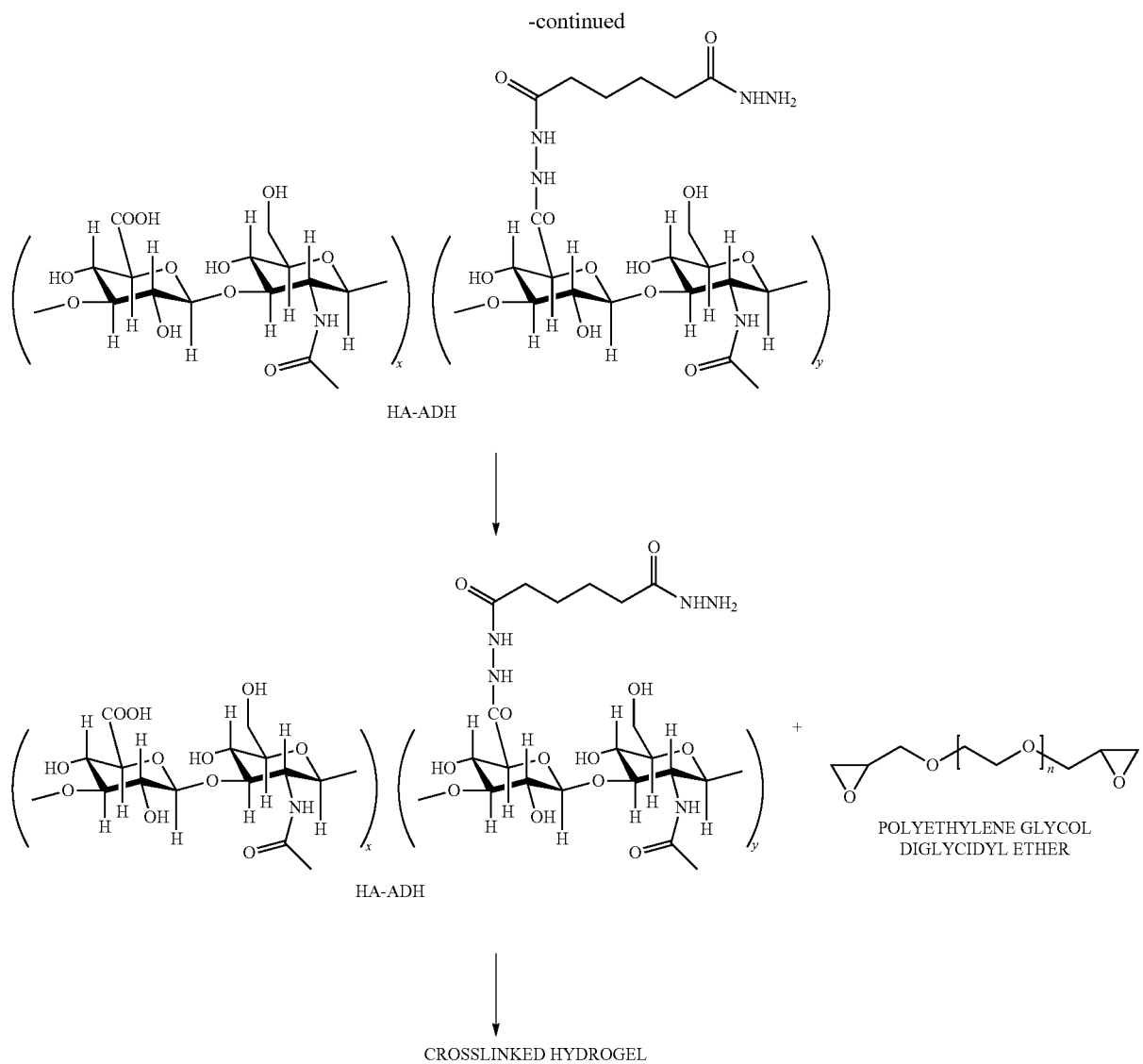

The gel precursors (in this case the HA-ADH and the PEGDE) can be mixed with loaded vesicles such loaded liposomes/loaded micelles/loaded nanoparticles as disclosed above and then crosslinked. The crosslinking process is performed via chemical- or photo crosslinking. The crosslinking process is performed at any suitable temperature. Preferably, it is performed at ambient temperature. Preferably, it is performed at a temperature ranging from 20° C. to 25° C. The advantage of this feature is that the proteins/nucleic loaded in the vesicles are not denatured.

Vesicles according to the invention can be liposomes, micelles preferably of self-assembling amphipilic molecules or particles selected from nanoparticles and microparticles as disclosed above.

The loaded vesicles may be provided in a solution or in a suspension. The solvent may be selected in dependence of the vesicles. Solvent may be for example water or ethanol. Preferably, the solvent is water.

The HA used according to the present invention is a HA in a form suitable to form a hydrogel. It can be named as HA hydrogel precursor. Hence, the HA hydrogel precursor may be a functionalized HA. In an aspect, any HA functionalized for the purpose to be crosslinked can be used in the process of the present invention. Preferably, HA-ADH, HA-MA, HA-SH are used in the method of the invention. The cross-linkable functionalized HA can be added to the solution/suspension of the loaded vesicles as freeze dried functionalized HA or as a solution.

Crosslinkers suitable for the preparation of a HA hydrogel may be added to the solution/suspension containing the loaded vesicles and the functionalized HA. The method of the invention envisages the use of any crosslinkers suitable for the preparation of HA hydrogel. Preferred cross-linkers are (BDG), butanediol diglycidyl ether (BDDGE) or poly (ethyleneglycol) diglycidyl ether (PEDGE). More preferred cross-linker id PEGDE.

Once the solution/suspension comprising the loaded vesicles is mixed with the HA hydrogel precursors, the crosslinking reaction is induced. The crosslinking reaction can be a chemical crosslinking reaction such as a condensation or addition reaction or a radical polymerization (crosslinking). Radical polymerization may be initiated by light (photo-crosslinking), temperature or redox-reaction, preferably the radical polymerization is a photo crosslinking. Preferably, the photo crosslinking is a UV crosslinking reaction.

Typically, the preparation of HA hydrogel in the presence of PEDGE and HA-ADH is a chemical crosslinking reaction. Typically, the preparation of HA hydrogel in the presence HA-MA and no additional crosslinker is a photo-crosslinking reaction. The photo-crosslinking may require the presence of a photo initiator. The photo initiator may be mixed to the HA-hydrogel precursor before adding it the solution/suspension of the loaded vesicles. Alternatively, the HA hydrogel precursors and the photo-initiator may be added sequentially or simultaneously to the solution comprising the loaded vesicles. The photo crosslinking reaction is then started by exposing the solution/suspension comprising the loaded vesicles, the HA hydrogel precursor and the photo-initiator to a suitable radiation. Photo-initiators according to the present invention is preferably Irgacure 2959 of formula

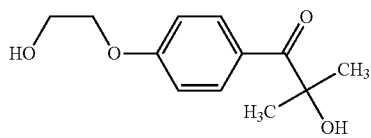

Irgacure 2959

Figure 5:
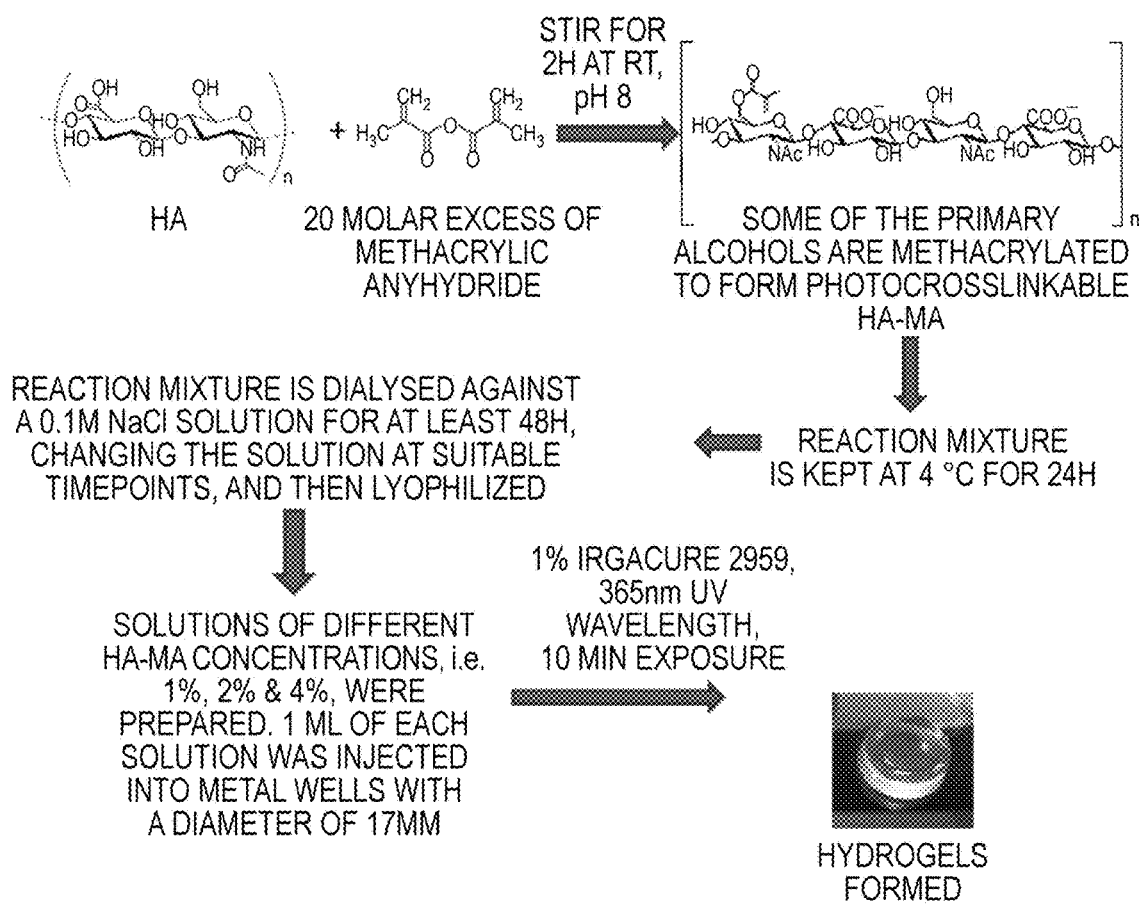
FIG. 5 is a scheme of the process for preparing HA hydrogel with dispersed loaded vesicles using photocrosslinkable HA-MA.

An exemplificative scheme of the photo-crosslinking HA hydrogel preparation using HA-MA is reported in FIG. 5.

Method of Administration

Pharmaceutical formulations comprising the HA hydrogel of the invention can be prepared accordingly with the suitable excipient(s) in dependence of the method of administration. Suitable pharmaceutical formulations can be in the form of tablet, capsules, solution such as injectable solution, suspension, cream.

The HA hydrogel formulation discussed above can be administered by injection, and more specifically by subcutaneous, intradermal, intraocular or intramuscular injection, orally or topically. They may also be delivered locally (e.g. intraspinal or intratumoral) in the treatment of cancer. The HA hydrogel of the invention contains an effective amount of drug, protein or peptide or nucleic acid. Exact dosages will vary depending on patient factors such as age, sex, general condition, and the like. Those of skill in the art can readily take these factors into account and use them to establish effective therapeutic concentrations without resort to undue experimentation.

HA hydrogel according to the invention can be advantageously prepared in situ. In other words, the crosslinking can occur just before the application of the hydrogel on the site of interest.

The hyaluronic acid (HA) hydrogel according to the invention and as disclosed above delivers drugs or proteins or peptides or nucleic acids at a controlled rate for several clinical and surgical applications, including but not limited to ophthalmology (e.g. glaucoma, corneal, ocular inflammatory, vitreoretinal and medical retinal diseases) and dermatological conditions.

Definitions

The term "$C_{10}$-$C_{22}$ alkyl" as used herein, refer to saturated, straight- or branched-chain hydrocarbon radicals containing between 10 and 22 carbon atoms, or the like, respectively. Examples of $C_{10}$-$C_{22}$ alkyl radicals include, but are not limited to $C_{10}$, $C_{12}$ such lauryl radicals, $C_{14}$, $C_{16}$ radicals.

EXAMPLES

Example 1: Preparation of Latanoprost-Loaded Liposomes: Extending the Duration of Release of an Anti-Glaucoma Drug, Latanoprost (Ltp)

Ltp is a hydrophobic drug. To make Ltp loaded EPC liposomes, 0.5 mM concentration of Ltp and 10 mm EPC were dissolved in a solvent mixture of 2:1 (v/v) ratio of chloroform:methanol in a round bottom flask (drug to lipid ratio of 0.05). The drug-lipid solution was manually mixed and the solvents were removed from the flask using a rotary evaporator maintained at 40° C. water bath for 2 hrs. A thin, dried drug-lipid film was obtained and this film was hydrated using PBS (pH7.4) buffer. The film was hydrated completely by manual shaking in a water bath maintained at 60° C. for 10-15 mins to form multilamellar vesicles (MLVs). MLVs suspension was extruded 15 times through polycarbonate filters of size 0.2 μm and 0.08 μm fitted on to a bench top extruder to obtain Ltp loaded large unilamellar vesicles (LUVs) of EPC (size~100 nm).

Example 2: Preparation of Methacrylate HA (HA-MA)+Ltp Loaded EPC Solution 20 mg or 40 mg of freeze-dried HA-MA was taken and dissolved directly in 1 ml of Ltp loaded EPC liposome suspension and allowed to stir overnight at room temperature to prepare 2% (w/v) or 4% HA-MA solution respectively.

Example 3: Preparation of Adipic Dihydrazide HA (HA-ADH)+Ltp Loaded EPC Solution 40 mg of freeze dried HA-ADH was taken and dissolved directly in 1 ml of Ltp loaded EPC liposome suspension and allowed to stir overnight at room temperature to prepare 4% (w/v) HA-ADH solution.

Example 4: Preparation of Chitosan/5-FU Nanoparticles by Ionotropic Gelation

Materials:
Chitosan 100 kDa (US sample), Chitosan (Sigma: 20-200 cps), Sodium tripolyphosphate (TPP), hydrophilic drug (5-FU)

Equipments:

IKA overhead stirrer, Magnetic stirrer, Thermo Centrifuge, Ultracentrifuge

Protocol I:

Prepare 1 mg/mL chitosan-5FU (hydrophilic drug) solutions in 1% acetic acid and filter using 0.22 μm filter (100 mL)

Prepare Triphenylphosphine (TPP) concentration 0.5 mg/mL in ultra pure water and filter using 0.22 μm filter (50 mL)

Adjust the pH of chitosan solution to 4.6 to 4.8 by adding 5M NaOH

Add TPP solution drop wise to chitosan solution under stirring at 1200 rpm using IKA over head stirrer in 30 min and continue stirring for 30 min.

Centrifuge the solution at 25000 rpm, re-disperse the pellet and measure the size using Malvern zeta sizer.

Observations:

In all the batches prepare following the above protocol around 90% particles have the size range 50 to 140 nm.

Example 5: HA Hydrogel with and without Ltp-EggPC Liposome-Chemical Crosslinking EggPC is a lipid that forms liposomes. Latanoprost (Ltp) was loaded into eggPCs using standard methods described in the literature. These liposomes were then mixed with HA-ADH and the epoxy crosslinker PEGDE, and allowed to set overnight. Release of latanoprost was then quantified. HA Hydrogel with a load of Latanoprost (no liposome) was prepared. Release of latanoprost was then quantified.

Figure 4:
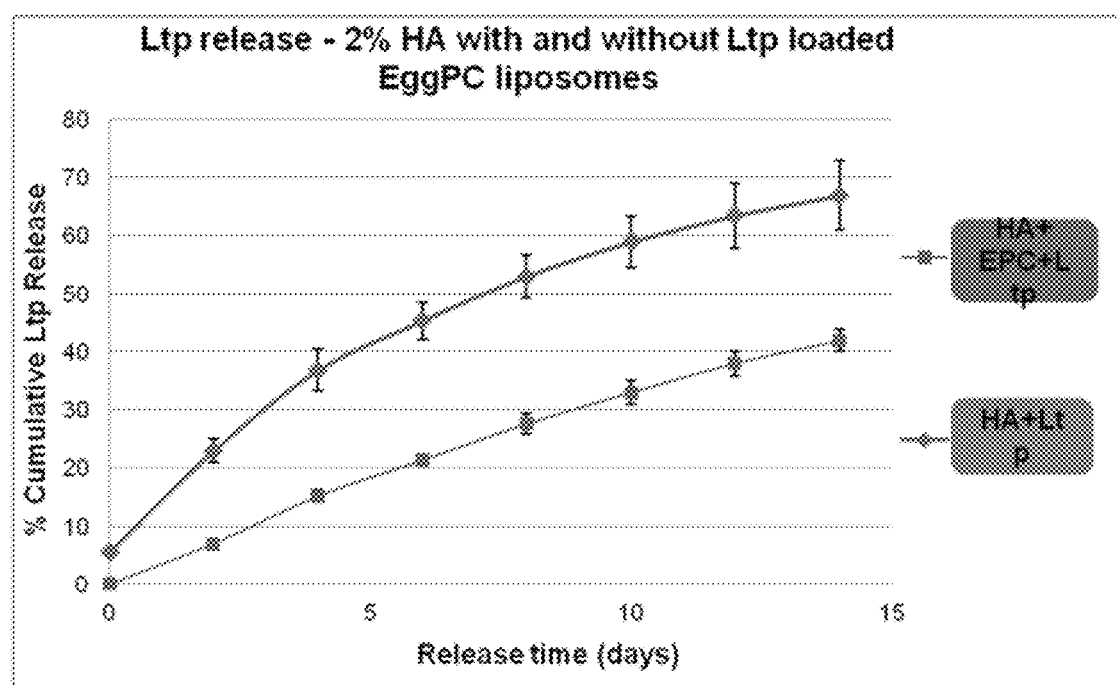
FIG. 4 is a plot illustrating the % cumulative latanoprost (Ltp) release in HA hydrogel with and without Ltp loaded in Egg liposomes.

The cumulative Ltp release from the HA-hydrogel with and without liposome was measured. The results are reported in FIG. 4.

Clearly, the latanoprost-loaded liposomes release drug more slowly than the drug directly dispersed in the hydrogel.

Example 6: PLGA Microparticles Based System for Sub-Conjunctival Controlled Release of 5-FU PLGA microparticles loaded with 5-FU were prepared by double emulsion technique. The microparticles were then lyophilized and dispersed in a HA precursors solution (HA-MA). Irgacure was used as initiator. UV crosslinking followed to give HA hydrogel with 5-FU loaded PLGA microparticles dispersed therein. The Batches formulations are disclosed in Table 1:

| Batch Formulation | I V | pH Of PVA | % Yield | % Loading | % EE |
|---|---|---|---|---|---|
| Batch 11 - 400 mg PLGA + 20 mg 5Fu (40% PLGA) | 0.4E | 1.7 | 51.25 | 2.0 | 39.4 |
| Batch 10- 300 mg PLGA + 20 mg 5Fu (30% PLGA) | 0.4E | | 41.67 | 3.5 | 52.2 |
| Batch 6 - 200 mg PLGA + 20 mg 5Fu (20% PLGA) | 0.4 | | 20 | 3.7 | 37 |

Figure 7:
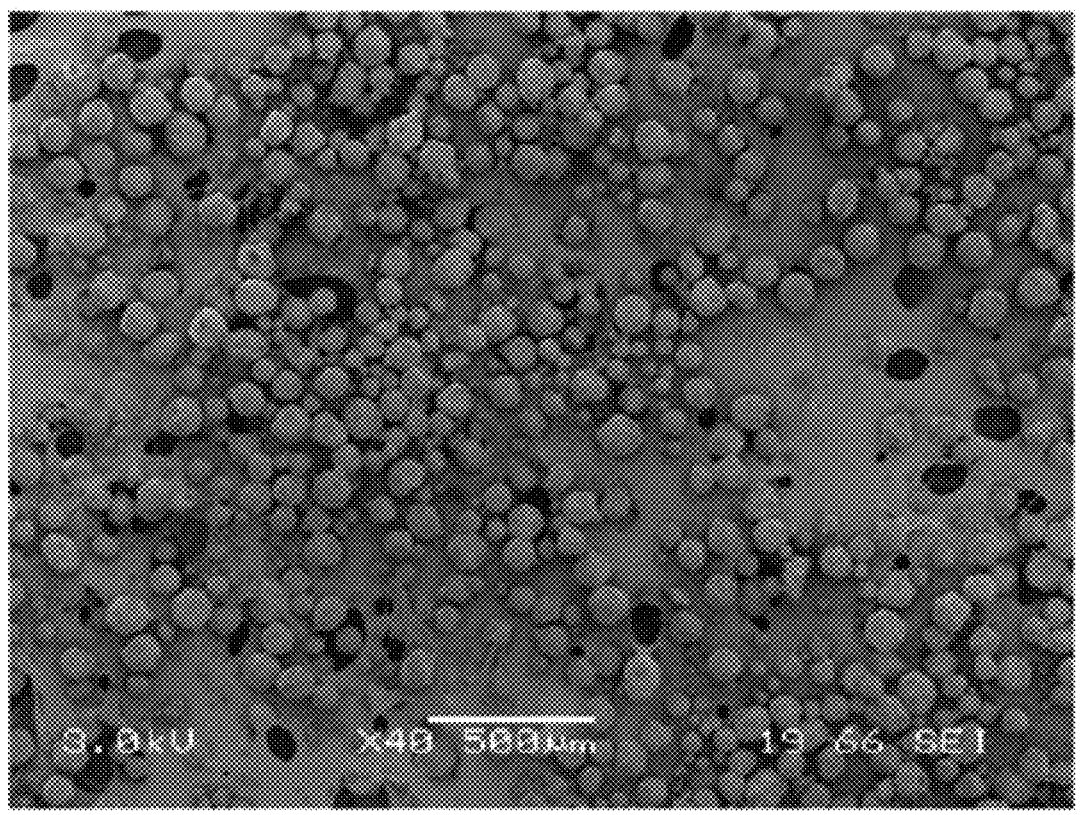
FIG. 7 shows a SEM image of PLGA microparticles loaded with 5-FU showing the particle size and the sphericity.

FIG. 7 report the SEM images of the microparticles obtained.

Figure 8:
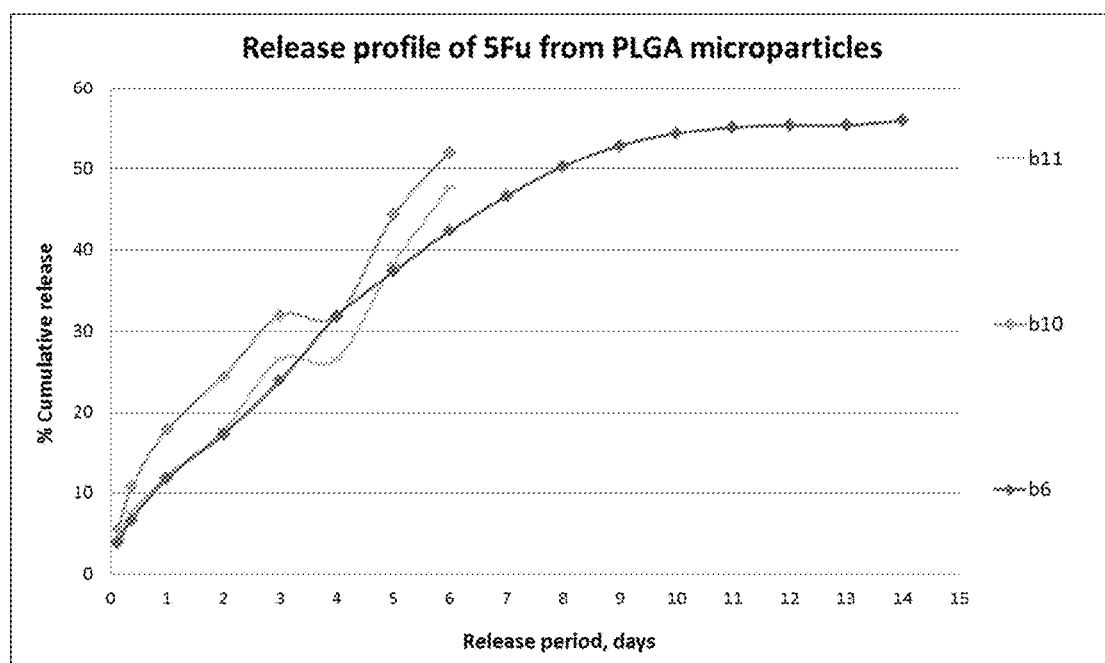
FIG. 8 shows the release profile of 5-FU from PLGA microparticles of batches 10, 11 and 6 in HA hydrogel.

FIG. 8 shows the release profile of the three batches over a period of 15 days.

Figure 9:
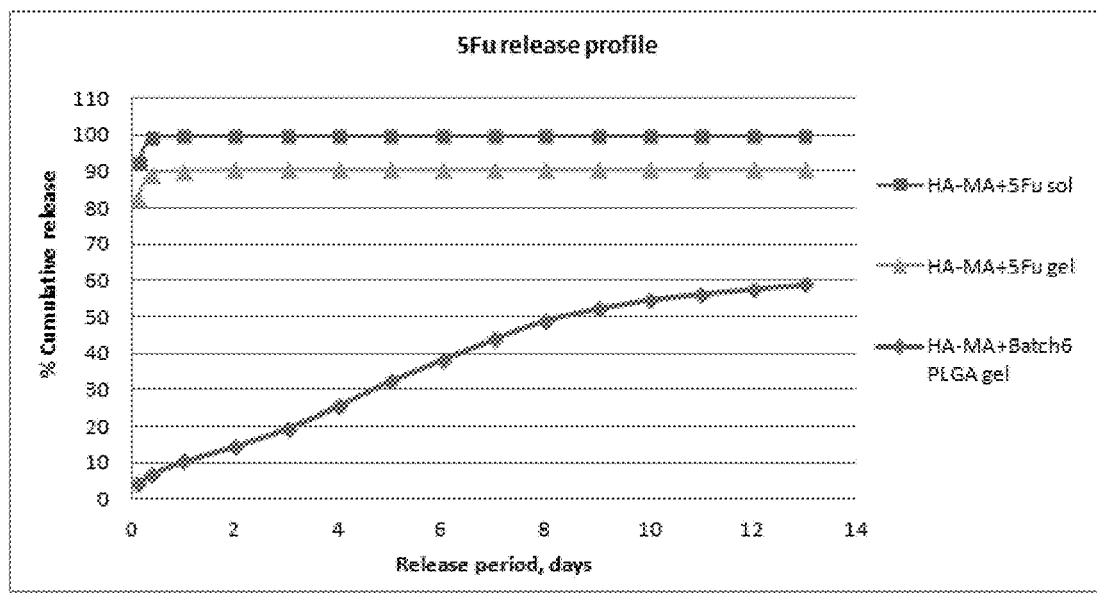
FIG. 9 shows the comparison of % cumulative release of 1) HA-MA+5FU sol, 2) HA-MA+5-FU gel and 3) HA-MA+PLGA/5 FU batch 6 microparticles.

Batch 6 hydrogel was then compared with a formulation of 5-FU dispersed in HA-MA hydrogel (5-FU free/no particle) and 5-FU dispersed in HA-MA sol. It can be clearly seen that the incorporation of the PLGA microparticles loaded with 5-FU retard the release of the drug. (FIG. 9) In particular, FIG. 9 shows the complete release of 5-FU in a couple of days if loaded into sol (no X-link) or from the crosslinked gel.

Example 7: UV Crosslinkable Hydrogels

Figure 6:
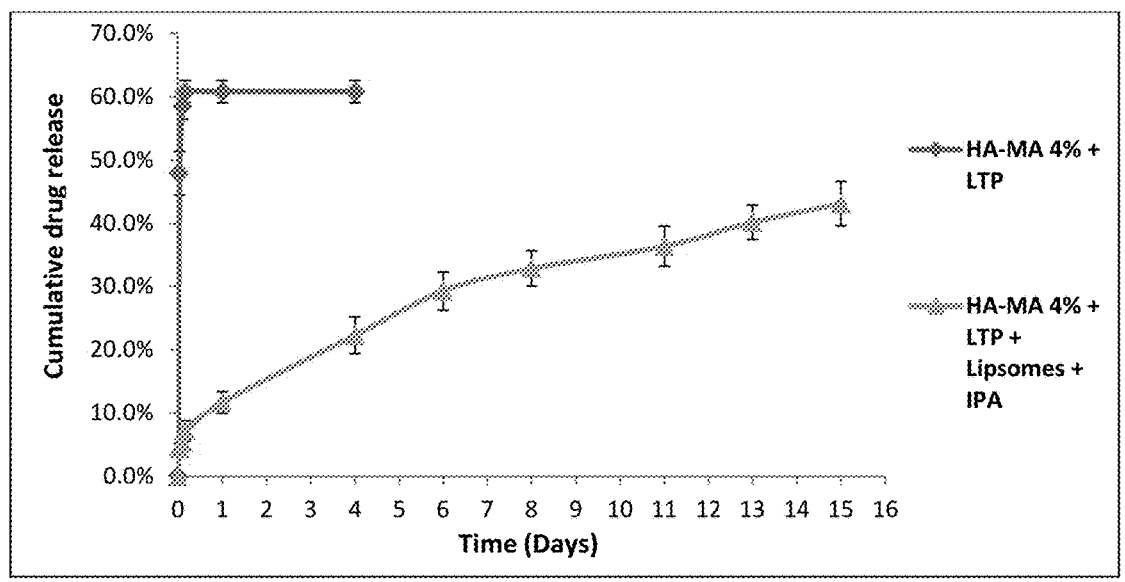
FIG. 6 shows the % cumulative drug release over 15 days of a HA-MA hydrogel at 4% wherein the Ltp is directly loaded (no vesicles) vs. HA-MA hydrogel 4% according to the present invention i.e. with Ltp loaded liposomes.

The hydrophobic drug was incorporated into the gel prior to crosslinking, and its release profile measured. In addition, liposomes containing the same hydrophobic drug were also incorporated into the gel precursors prior to crosslinking, and the consequent release profile also quantified. In particular latanoprost was used as a drug and HA-MA was used as HA functionalized moiety. The hydrogel is a 4% (w/v) HA-MA hydrogel. The data are shown in FIG. 6.

It can be clearly seen that incorporation of liposomes into the hydrogel retards the release of the drug, and leads to an almost linear (ideal) release profile over 2 weeks. This principle can be applied to hydrophobic drugs incorporated first into liposome/micelle and then into the hydrogel.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A hyaluronic acid (HA) hydrogel comprising loaded liposomes dispersed therein
   wherein
   the loaded liposomes are loaded with one or more hydrophobic drugs;
   the hyaluronic acid hydrogel is a covalently crosslinked hydrogel; and
   the crosslinked hydrogel comprises at least one crosslinker selected from the group consisting of butylene glycol diglycidyl ether (BDG), butanediol diglycidyl ether (BDDGE) and poly(ethyleneglycol) diglycidyl ether (PEGDE), wherein the HA may optionally be functionalized; and
wherein the incorporation of liposomes into the hydrogel retards the release of the drug and leads to an almost linear drug release profile over two weeks.

2. The HA hydrogel according to claim 1 wherein the HA is functionalized.

3. The HA hydrogel according to claim 1 wherein the functionalized HA is selected from the group consisting of methacrylate-HA (HA-MA), adipic acid dihydrazide HA (HA-ADH), lactic acid HA (MeLAHA) and caprolactone HA (MeCLHA).

4. The HA hydrogel according to claim 1 wherein the crosslinker is poly(ethyleneglycol) diglycidyl ether (PEGDE).

5. The HA hydrogel according to claim 1 wherein the HA hydrogel is selected from a HA-ADH crosslinked with PEGDE-hydrogel, HA-MA crosslinked with PEGDE hydrogel.

6. The HA hydrogel according to claim 1 wherein the amount of loaded vesicles dispersed in the HA hydrogel is the 1% to the 40% by weight of the whole HA hydrogel.

7. The HA hydrogel according to claim 2, wherein when the functionalized HAs functionalized for crosslinking are interconnected by crosslinkers the moles of crosslinker are 2 to 10 times the mole of effectively functionalized HA.

8. The HA hydrogel of claim 1 wherein the liposomes are EggPC liposomes.

9. The HA hydrogel according to claim 1 wherein the hydrophobic drug is selected from the group consisting of an antibiotic drug, a chemio-therapeutic drug, and a drug for the treatment of glaucoma or ocular hypertension.

10. The HA hydrogel of claim 1, wherein the hydrophobic drug is selected from the group consisting of ciprofloxacin, paclitaxel, doxorubicin, and latanoprost.

11. The HA hydrogel of claim 1, wherein the liposome is an EggPC liposome and wherein the hydrophobic drug is latanoprost.

12. The HA hydrogel of claim 11 wherein the functionalized HA is HA-ADH and wherein the HA hydrogel is crosslinked with PEGDE.

13. A pharmaceutical formulation comprising the HA hydrogel as defined in claim 1.

14. The pharmaceutical formulation of claim 13 adapted for administration selected from the group consisting of oral, topical, intravenous, subcutaneous and intramuscular administration.

15. A method for preparing the HA hydrogel as defined in claim 1 comprising:
a) providing functionalized HA;
b) crosslinking the functionalized HA in the presence of at least one crosslinker,
wherein
the at least one crosslinker is selected from the group consisting of buthylene glycol diglycidyl ether (BDG), butanediol diglycidyl ether (BDDGE) and poly(ethyleneglycol) diglycidyl ether (PEGDE); and
the crosslinking occurs in the presence of liposomes loaded with at least one hydrophobic drug.

* * * * *